US009811902B2

(12) United States Patent
Flohr et al.

(10) Patent No.: US 9,811,902 B2
(45) Date of Patent: Nov. 7, 2017

(54) DETERMINING A VALUE OF A RECORDING PARAMETER BY USE OF AN ANATOMIC LANDMARK

(71) Applicant: Siemens Aktiengesellschaft, Munich (DE)

(72) Inventors: Thomas Flohr, Uehlfeld (DE); Michael Scheuering, Nuremberg (DE); Bernhard Schmidt, Fuerth (DE); Martin Sedlmair, Zirndorf (DE); Grzegorz Soza, Heroldsberg (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 105 days.

(21) Appl. No.: 14/511,381

(22) Filed: Oct. 10, 2014

(65) Prior Publication Data
US 2015/0104092 A1 Apr. 16, 2015

(30) Foreign Application Priority Data
Oct. 14, 2013 (DE) .......................... 10 2013 220 665

(51) Int. Cl.
*G06T 7/00* (2017.01)
*A61B 6/00* (2006.01)
(Continued)

(52) U.S. Cl.
CPC ............ *G06T 7/0012* (2013.01); *A61B 6/032* (2013.01); *A61B 6/08* (2013.01); *A61B 6/4447* (2013.01);
(Continued)

(58) Field of Classification Search
CPC ......... A61B 6/032; A61B 6/08; A61B 6/4447; A61B 6/4482; A61B 6/465; A61B 6/469;
(Continued)

(56) References Cited

U.S. PATENT DOCUMENTS

| 5,379,333 A * | 1/1995 | Toth ...................... A61B 6/032 378/108 |
| 6,507,639 B1 * | 1/2003 | Popescu ................. A61B 6/032 378/108 |

(Continued)

FOREIGN PATENT DOCUMENTS

| CN | 1758876 A | 4/2006 |
| CN | 1895170 A | 1/2007 |

(Continued)

OTHER PUBLICATIONS

Jakel et al., "Selection of beam angles for radiotherapy of skull base tumours using charged particles", Phys. Med. Biol. 45 (2000) 1229-1241.*

(Continued)

*Primary Examiner* — Katrina Fujita
(74) *Attorney, Agent, or Firm* — Harness, Dickey & Pierce, P.L.C.

(57) ABSTRACT

A method and an imaging system are disclosed. The method, for determining at least one value of at least one recording parameter for a recording of an X-ray image of a patient positioned on an examination table, uses contactless scanning of at least part of the surface of the patient via at least one electromagnetic sensor, to calculate the three-dimensional contour of the scanned surface without additional exposure to radiation. At least one anatomic landmark of the patient can be identified using the three-dimensional contour, and the position of the anatomic landmark is determinable in the coordinate system of the table. The value of the recording parameter is determinable using the position of the anatomic landmark. The value of the recording parameter is determinable quickly and easily since contactless scanning of surfaces can be achieved quickly and easily in terms of technology.

20 Claims, 4 Drawing Sheets

(51) Int. Cl.
*G06K 9/46* (2006.01)
*G06T 17/00* (2006.01)
*A61B 6/03* (2006.01)
*A61B 6/08* (2006.01)
*G06T 7/73* (2017.01)

(52) U.S. Cl.
CPC ............. *A61B 6/465* (2013.01); *A61B 6/469* (2013.01); *A61B 6/545* (2013.01); *G06K 9/4604* (2013.01); *G06T 7/73* (2017.01); *G06T 17/00* (2013.01); *A61B 6/4482* (2013.01); *A61B 6/501* (2013.01); *G06T 2207/10081* (2013.01)

(58) Field of Classification Search
CPC ....... A61B 6/501; A61B 6/545; G06T 7/0012; G06T 7/73; G06T 17/00; G06T 2207/10081; G06K 9/4604
See application file for complete search history.

(56) References Cited

U.S. PATENT DOCUMENTS

| | | | | |
|---|---|---|---|---|
| 7,267,482 B2 * | 9/2007 | Ohishi | ................. | A61B 6/4441 378/196 |
| 7,466,849 B2 * | 12/2008 | Haider | ..................... | A61B 6/00 382/128 |
| 7,508,967 B2 * | 3/2009 | Harari | .................... | A61N 5/103 378/65 |
| 7,715,522 B2 * | 5/2010 | Goto | ...................... | A61B 6/032 378/16 |
| 7,869,562 B2 * | 1/2011 | Khamene | ................. | A61B 6/08 209/207 |
| 9,299,148 B2 * | 3/2016 | Liu | ....................... | G06T 7/0032 |
| 2003/0147495 A1 * | 8/2003 | Kato | ...................... | A61N 5/103 378/65 |
| 2005/0111621 A1 * | 5/2005 | Riker | ................... | A61N 5/1031 378/65 |
| 2006/0198499 A1 | 9/2006 | Spies | | |
| 2008/0064953 A1 | 3/2008 | Falco et al. | | |
| 2008/0101538 A1 * | 5/2008 | Schliermann | ............ | A61B 6/08 378/95 |
| 2008/0310582 A1 * | 12/2008 | Flohr | ..................... | A61K 49/04 378/5 |
| 2009/0226060 A1 * | 9/2009 | Gering | .................... | G06T 7/174 382/128 |
| 2010/0104068 A1 * | 4/2010 | Kilby | ................... | A61N 5/1031 378/65 |
| 2011/0044429 A1 * | 2/2011 | Takahashi | .............. | A61N 5/103 378/65 |
| 2011/0129058 A1 | 6/2011 | Ulrici et al. | | |
| 2011/0129060 A1 * | 6/2011 | Handa | .................... | A61B 6/022 378/9 |
| 2011/0142316 A1 * | 6/2011 | Wang | ..................... | G06T 11/006 382/131 |
| 2011/0268244 A1 * | 11/2011 | Handa | .................... | A61B 6/022 378/4 |
| 2012/0014579 A1 * | 1/2012 | Li | .......................... | A61B 6/032 382/131 |
| 2012/0230470 A1 * | 9/2012 | Bertram | ................. | A61B 6/032 378/98.5 |
| 2012/0294504 A1 * | 11/2012 | Kyriakou | ............. | A61B 6/5247 382/132 |
| 2012/0310615 A1 * | 12/2012 | Moore | ................ | G06F 19/3437 703/11 |
| 2012/0312961 A1 * | 12/2012 | Raleigh | .................... | A61B 6/12 250/206 |
| 2013/0083004 A1 * | 4/2013 | Nord | ..................... | A61N 5/1031 345/419 |
| 2013/0083894 A1 * | 4/2013 | Niebler | ................. | A61B 6/4441 378/62 |
| 2013/0131431 A1 * | 5/2013 | Tsukuda | ................ | A61N 5/1049 600/1 |
| 2013/0172734 A1 * | 7/2013 | Hsieh | ...................... | A61B 6/032 600/425 |
| 2013/0324784 A1 * | 12/2013 | Fredriksson | ......... | A61N 5/1031 600/1 |
| 2013/0345543 A1 * | 12/2013 | Steibel, Jr. | .............. | A61B 6/467 600/407 |
| 2015/0196267 A1 * | 7/2015 | Ohishi | ................. | A61B 6/4441 378/20 |
| 2015/0366527 A1 * | 12/2015 | Yu | .......................... | A61B 5/055 382/131 |

FOREIGN PATENT DOCUMENTS

| | | |
|---|---|---|
| CN | 101346102 A | 1/2009 |
| CN | 103079470 A | 5/2013 |
| DE | 102012201798 A1 | 8/2013 |
| KR | 20110050656 A | 5/2011 |
| WO | WO 2012023088 A1 | 2/2012 |

OTHER PUBLICATIONS

Wang et al., "Optimization of beam orientations and beam weights for conformal radiotherapy using mixed integer programming", Phys. Med. Biol. 48 (2003) 4065-4076.*

Zhang et al., "Peak Skin and Eye Lens Radiation Dose From Brain Perfusion CT Based on Monte Carlo Simulation", American Journal of Roentgenology 198.2 (2012): 412-417.*

Zhang et al., "Three-dimensional reconstruction in free-space whole-body fluorescence tomography of mice using optically reconstructed surface and atlas anatomy", Journal of biomedical optics 14.6 (2009): 064010-064010.*

German Priority Application DE 102013220665.8 filed on Oct. 14, 2013.

German Office Action for Priority Application DE 102013220665.8 dated May 22, 2014.

Korean Office Action and English translation thereof dated Nov. 13, 2015.

Chinese Office Action and English translation thereof dated Aug. 2, 2016.

Chinese Office Action and English translation thereof dated Aug. 10, 2017.

* cited by examiner

DETERMINING A VALUE OF A RECORDING PARAMETER BY USE OF AN ANATOMIC LANDMARK

PRIORITY STATEMENT

The present application hereby claims priority under 35 U.S.C. §119 to German patent application number DE 102013220665.8 filed Oct. 14, 2013, the entire contents of which are hereby incorporated herein by reference.

FIELD

At least one embodiment of the invention generally relates to a method and/or to an imaging system for determining a value of a recording parameter.

BACKGROUND

Computed tomography (CT) is an imaging method which is primarily used for medical diagnosis. In CT an X-ray source and an X-ray detector that cooperates with the X-ray source rotate about a patient positioned on an examination table. Images are taken at various angular positions of X-ray source and X-ray detector, wherein the patient can be moved along the axis of rotation, and this is also called the system axis. The individual images are each a projection of a region of the patient to be recorded. The angular position of X-ray source and X-ray detector is therefore also called the angle of projection. At the end of the series of images, which is also called a "scan", the projections are processed in such a way that a three-dimensional (3D), tomographic X-ray image is produced. Therefore carrying out a series of images will also be called a tomographic recording below. The recording of an X-ray image also comprises recording a single projection or a plurality of projections which are each recorded at the same angle of projection, however. An X-ray image can also hereinafter be taken to mean an overview image in the form of what is referred to as a topogram in particular.

The quality of the X-ray image is influenced by the choice of values of the recording parameters crucial to recording of the X-ray image. A scanning protocol comprises values for recording parameters which determine the exact progress of the tomographic recording of an X-ray image. A scanning protocol can also include values for recording parameters which influence the subsequent reconstruction of an X-ray image. The recording parameters can be by way of example the dose to be applied or intensity values of the X-ray radiation. Such intensity values can be modulated so as to be dependent on the projection angle in particular. The recording parameters can also include settings for filters or screens and the start and end positions of the examination table. In the medical environment the selection of suitable recording parameters is important in order to avoid unnecessary exposure of the patient to radiation as well as for the quality of the resulting X-ray image. Such recording parameters are often determined by selection of a pre-defined scanning protocol or they are created on the basis of analysis of a topogram. However, recording of a topogram constitutes exposure to radiation for the patient; furthermore, only limited information about the surface contour of the patient may be attained with a topogram.

SUMMARY

At least one embodiment of the invention is directed to determining a value of a recording parameter for recording an X-ray image with optimally low exposure to radiation for the patient and in a manner that is quick and easy in terms of technology.

A method and an imaging system are disclosed.

At least one embodiment of the system and method will be discussed below. Features, advantages or alternative embodiments mentioned in this connection are likewise to be transferred to the other claimed subject matters, and vice versa. In other words, the claims in question (which are directed by way of example toward a system) can also be developed by the features that are described or claimed in connection with a method. The corresponding functional features of the method are formed by corresponding representational modules.

An embodiment of the inventive method is for determining at least one value of at least one recording parameter for a recording of an X-ray image of a patient positioned on an examination table uses contactless scanning of at least part of the surface of the patient by use of at least one electromagnetic sensor, in order to calculate the three-dimensional contour of the scanned surface without additional exposure to radiation. The inventors have recognized that at least one anatomic landmark of the patient can be identified using the three-dimensional contour and the position of the anatomic landmark can be determined in the coordinate system of the examination table. The value of the recording parameter can be determined using the position of the anatomic landmark. Determining the value of the recording parameter in this way occurs quickly and easily in terms of technology since the contactless scanning of surfaces can be achieved quickly and easily in terms of technology. This applies in particular if the at least one electromagnetic sensor is constructed in the form of a stereo camera or a triangulation system or a range measuring system, or wherein the electromagnetic sensor is constructed for scanning a surface by way of structured illumination. The inventive method also has great flexibility since different recording parameters may be determined using the position of the anatomic landmark.

The landmark can in particular be a body region of the patient, i.e. by way of example the head, eyes, thorax, chest, legs or a single knee joint. In at least one embodiment of the invention determining the position of the landmark also includes determining the position of a plurality of identified landmarks relative to each other. A conclusion can also be drawn about the identity and position of further landmarks using landmarks already identified and whose position has been determined. By way of example, a conclusion about the position of the heart or a lung can be drawn using the determination of the position and orientation of the thorax.

At least one embodiment of the invention can also be implemented in the form of an imaging system. At least one embodiment of the imaging system comprises an X-ray apparatus, in particular a CT apparatus with a tiltable gantry, for recording an X-ray image of a patient positioned on an examination table, and comprising at least one electromagnetic sensor, and comprising a computer with an arithmetic logic unit, wherein the arithmetic logic unit is designed to carry out at least one embodiment of the inventive method via execution of a computer program stored on a data carrier or on the memory of the computer. The at least one electromagnetic sensor can be by way of example a stereo camera or a triangulation system or a range measuring system, or the electromagnetic sensor can be constructed for scanning a surface by way of structured illumination. The at least one electromagnetic sensor can in particular be constructed as part of the CT apparatus or be positioned without a permanent connection to the CT apparatus. The at least one electromagnetic sensor is advantageously positioned in such a way that the depth information obtained by contactless scanning is optimally homogeneous.

BRIEF DESCRIPTION OF THE DRAWINGS

The invention will be described and explained in more detail below with reference to the example embodiments illustrated in the figures, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the inventive method is for determining at least one value of at least one recording parameter for a recording of an X-ray image of a patient positioned on an examination table uses contactless scanning of at least part of the surface of the patient by use of at least one electromagnetic sensor, in order to calculate the three-dimensional contour of the scanned surface without additional exposure to radiation. The inventors have recognized that at least one anatomic landmark of the patient can be identified using the three-dimensional contour and the position of the anatomic landmark can be determined in the coordinate system of the examination table. The value of the recording parameter can be determined using the position of the anatomic landmark. Determining the value of the recording parameter in this way occurs quickly and easily in terms of technology since the contactless scanning of surfaces can be achieved quickly and easily in terms of technology. This applies in particular if the at least one electromagnetic sensor is constructed in the form of a stereo camera or a triangulation system or a range measuring system, or wherein the electromagnetic sensor is constructed for scanning a surface by way of structured illumination. The inventive method also has great flexibility since different recording parameters may be determined using the position of the anatomic landmark.

The landmark can in particular be a body region of the patient, i.e. by way of example the head, eyes, thorax, chest, legs or a single knee joint. In at least one embodiment of the invention determining the position of the landmark also includes determining the position of a plurality of identified landmarks relative to each other. A conclusion can also be drawn about the identity and position of further landmarks using landmarks already identified and whose position has been determined. By way of example, a conclusion about the position of the heart or a lung can be drawn using the determination of the position and orientation of the thorax.

According to a further advantageous aspect of at least one embodiment, the inventive method comprises calculating a patient model using the three-dimensional contour for visual representation of the patient. A patient model of this kind can be easily modified, by way of example the corresponding visual representation can be made from various perspectives, so a user of an inventive imaging system or a person carrying out the treatment can take the information about the three-dimensional contour into account when planning the recording or further treatment.

According to a further advantageous aspect of at least one embodiment, the inventive method comprises highlighting the identified landmark in a visual representation of the patient. The user of an inventive imaging system or a person carrying out the treatment consequently has additional information available about the identity and position of the landmark in a particularly intuitive manner.

According to a further advantageous aspect of at least one embodiment, the inventive method comprises providing a graphic user surface with a button, wherein the button represents the identified landmark, wherein the button is designed to trigger determination of the value of the recording parameter by way of user interaction. According to a further aspect the button is designed to trigger recording of the X-ray image by way of user interaction. The inventive method can consequently be carried out particularly intuitively and quickly and the X-ray recording can be started particularly intuitively and quickly.

According to a further aspect of at least one embodiment, the inventive determination of the value of the recording parameter comprises automatic selection of a retrievably stored value of a recording parameter using the identity and/or position of the anatomic landmark. Such determination by way of automatic selection allows a plurality of recording parameters, and therewith entire scanning protocols, to be selected simultaneously in particular by way of classifying.

According to one advantageous aspect of at least one embodiment of the invention, the recording parameter comprises the applied dose for the recording of the X-ray image. The applied dose can be determined since the level of X-ray absorption by the patient in the various directions of radiation can also be calculated with the three-dimensional contour of the scanned surface. The applied dose can in particular be determined as a function of the projection angle, wherein such angle-dependent adjustment of the applied dose is also known as dose modulation. One advantage in the present invention with respect to conventional methods for dose modulation is that the contour of the patient can be determined particularly accurately, so there is an especially large amount of information available for calculation of the dose. A dose modulation may also be achieved by modulation of the emitted intensity of the X-ray radiation. The intensity values are achieved by way of example by controlling the X-ray source, i.e. by way of example by controlling the current or voltage of an X-ray tube.

According to a further advantageous aspect of at least one embodiment of the invention, the recording parameter comprises the volume of a contrast medium for a contrast medium-enhanced recording of the X-ray image, because the volume of a contrast medium to be administered also depends on the body weight of the patient. A conclusion can be drawn directly about the body weight of the patient using the three-dimensional contour of the patient.

According to a particularly advantageous aspect of at least one embodiment of the invention, the recording parameter comprises the position of the examination table for the recording of the X-ray image. If a specific region of the patient is to be recorded then the position of the region can be determined using the landmarks, in particular in the coordinate system of the examination table or an X-ray apparatus intended for recording of the X-ray image. The position of the examination table, in particular the start position and end position, is determined particularly precisely according to the invention. This determination of the position of the examination table is also particularly flexible since in the event of a movement the patient can be scanned again easily and without exposure to radiation and the position of the examination table can be determined again.

According to a further advantageous aspect of at least one embodiment of the invention, the recording parameter comprises the orientation of the patient. The orientation comprises in particular the relative orientation of head and feet with respect to the path of the examination table. However, orientation also comprises the position of the patient, i.e. by way of example supine position, right lateral position, left lateral position, prone position, etc. Quick and easy determination of the orientation or position of the patient allows further recording parameters, such as the dose to be applied, to be determined particularly quickly and easily. Determination of the orientation or position also serves as a check as to whether the patient is in the desired orientation or position.

According to a further advantageous aspect of at least one embodiment of the invention, the recording is a tomographic recording via a CT apparatus, wherein the CT apparatus comprises an X-ray source which can rotate about a system axis, wherein in a specific position of the examination table the system axis centrally penetrates a region of the patient which is to be recorded. The homogeneity of the quality of the X-ray image is consequently increased and the exposure to radiation for the patient is kept low while retaining the quality of the X-ray image.

According to a further aspect of at least one embodiment of the invention, the recording is a tomographic recording via a CT apparatus, wherein the CT apparatus has a tiltable gantry with an X-ray source which can be rotated about a system axis, wherein the anatomic landmark is a body region of the patient particularly sensitive to radiation, wherein the recording parameter comprises the angle of inclination of the gantry, wherein the angle of inclination is determined in such a way that the body region sensitive to radiation is not located, or is located only to a limited extent, in the beam path of the X-ray source. Exposure to radiation for the body region of the patient particularly sensitive to radiation is reduced thereby.

At least one embodiment of the invention can also be implemented in the form of an imaging system. At least one embodiment of the imaging system comprises an X-ray apparatus, in particular a CT apparatus with a tiltable gantry, for recording an X-ray image of a patient positioned on an examination table, and comprising at least one electromagnetic sensor, and comprising a computer with an arithmetic logic unit, wherein the arithmetic logic unit is designed to carry out at least one embodiment of the inventive method via execution of a computer program stored on a data carrier or on the memory of the computer. The at least one electromagnetic sensor can be by way of example a stereo camera or a triangulation system or a range measuring system, or the electromagnetic sensor can be constructed for scanning a surface by way of structured illumination. The at least one electromagnetic sensor can in particular be constructed as part of the CT apparatus or be positioned without a permanent connection to the CT apparatus. The at least one electromagnetic sensor is advantageously positioned in such a way that the depth information obtained by contactless scanning is optimally homogeneous.

Figure 1:
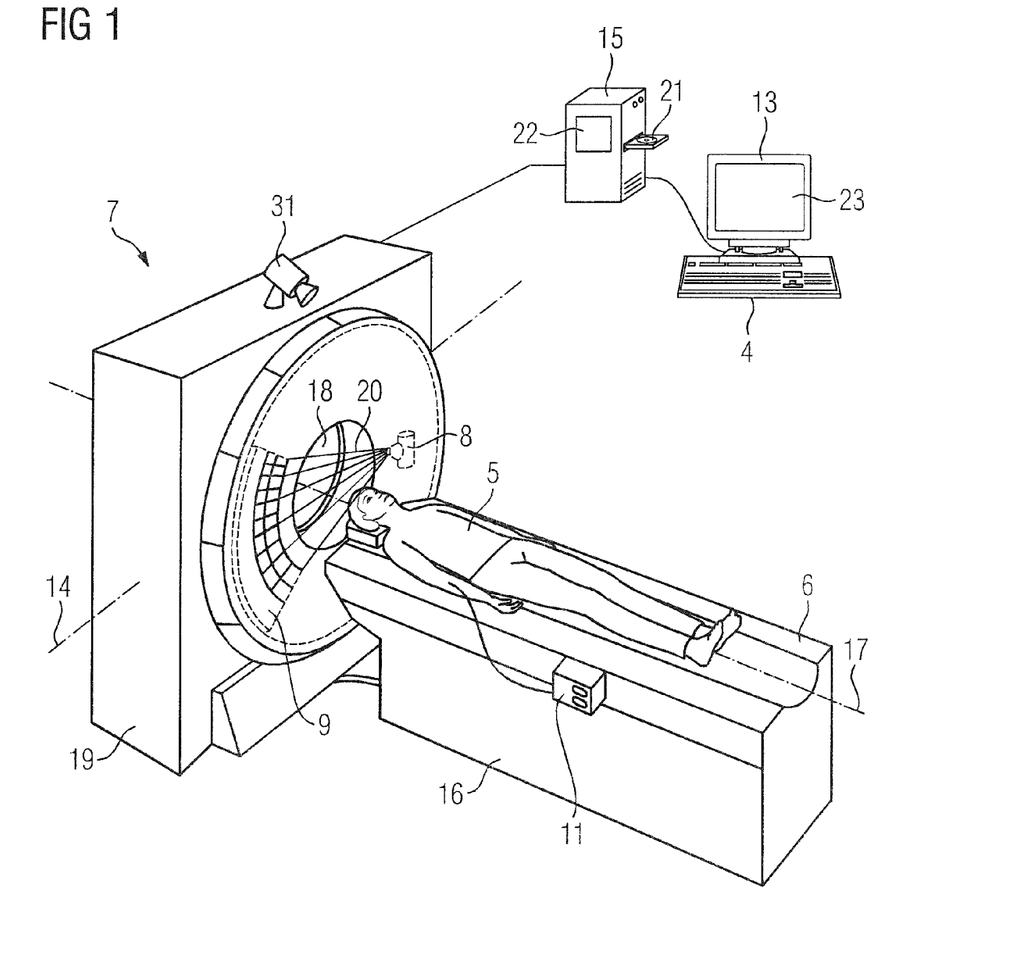
FIG. 1 shows an example of an embodiment of the inventive imaging system.

FIG. 1 shows an example inventive imaging system, comprising a CT apparatus. During the tomographic recording of an X-ray image the patient 5 lies on an examination table 6 which is connected to a table base 16 in such a way that it supports the examination table 6 with the patient 5. During a tomographic recording the examination table 6 moves the patient 5 in a spiral mode along a system axis 17 through the opening 18 in the gantry 19 of the CT apparatus 7. During this movement a large number of projection recordings of a body part of the patient 5 is created. During the tomographic recording of an X-ray image the X-ray detector 9 and the X-ray source 8, which cooperates with the X-ray detector 9, move about the system axis 17. X-ray source 8 and X-ray detector 9 are arranged in a gantry 19 in such a way that they oppose one another and the X-ray beams 20 of the X-ray source 8 are detectable for the X-ray detector 9. The X-ray detector 9 of a CT apparatus 7 shown here is a detector with a plurality of rows and columns.

The gantry 19 can be constructed so as to be tiltable about an axis, in particular about an axis perpendicular to the system axis 17. In the embodiment of the invention shown here the gantry 19 can be tilted about the tilting axis 14 running through the system axis 17, wherein the tilting axis 14 is oriented parallel to the earth's surface and perpendicular to the system axis 17. A tiltable gantry 19 is taken to mean a gantry 19 in which at least the rotatable part of the gantry 19, which also comprises the X-ray source 8 and the X-ray detector 9, is constructed so as to be tiltable. The rotatable part of the gantry 19 is also called the "drum". The CT apparatus can also have a frame 24, in which at least part of the gantry 19 is tiltably mounted.

An X-ray detector 9 is conventionally designed as a scintillation counter in which the high-energy X-ray photons are converted by way of a scintillator into low-energy photons in the optical spectrum and then detected by way of a photodiode. Alternatively the X-ray detector 9 can be designed as a directly converting detector which converts the high-energy X-ray photons by way of a semi-conductor material directly into an electrical signal current by internal photo excitation using the photovoltaic principle. The X-ray source 8 is conventionally an X-ray tube. In principle other X-ray sources 8, which are suitable for tomographic imaging, may also be used, however.

In a further embodiment the CT apparatus 7 has two mutually cooperating pairs of X-ray sources 8 and X-ray detectors 9 respectively, so the CT apparatus is particularly suitable for multiple-energy recordings. In an alternative embodiment (not shown here) the X-ray apparatus is a C-arm X-ray apparatus. Other types of X-ray source 8 and X-ray detector 9 in particular can be used in a C-arm X-ray apparatus. A flat detector by way of example can be used as the X-ray detector 9. The X-ray radiation in a CT apparatus 7 or a C-arm X-ray apparatus usually has a fan, pyramidal or conical shape auf. The X-ray radiation is typically shaped by way of a filter system.

In addition the embodiment of the CT apparatus 7 shown here also has a contrast medium injector 11 for injection of contrast medium into the circulation of the patient 5. The X-ray image can consequently be taken by way of a contrast medium in such a way that for example the vessels of the patient 5, in particular the ventricles of the beating heart, can be depicted with enhanced contrast. Contrast media are generally taken to mean agents which improve the depiction of structures and functions of the body in the imaging method. Within the framework of the application at hand contrast media are taken to mean conventional contrast media, such as iodine, and tracers, such as 18F, 11C or 13N.

An embodiment of the inventive imaging system also has at least one electromagnetic sensor 31 which is designed for contactless scanning of at least part of the surface of the patient 5. An electromagnetic sensor 31 is designed for the detection of electromagnetic radiation, in particular for the detection of electromagnetic radiation in a, compared to X-ray radiation, low-frequency spectral range, by way of example in the visible or infrared spectral range. The electromagnetic sensor 31 can therefore be one or more camera (s) or video camera(s). In the example shown here the electromagnetic sensor 31 is a 3D camera secured to the gantry and which is constructed by way of example as a stereo camera or as a range measuring system (known as a "time-of-flight camera"). In a further embodiment of the invention the electromagnetic sensor 31 is constructed for scanning a surface by way of structured illumination. In this embodiment the imaging system also has a lighting unit for generating structured illumination of at least part of the surface of the patient 5. Furthermore, the electromagnetic sensor 31 and the lighting unit are in this case positioned in such a way and constructed in terms of their emission or detection properties such that the electromagnetic sensor 31 is constructed for detection of the radiation reflected by the surface of the patient 5.

In a further embodiment of the invention the electromagnetic sensor 31 is permanently integrated in the gantry 19 of the CT apparatus 7. In an alternative embodiment the electromagnetic sensor 31 is integrated in the rotatable part of the gantry 19 in such a way that the electromagnetic sensor 31 rotates with the X-ray source 8 and with the X-ray detector 9 during recording. The surface of the patient 5 can consequently be scanned particularly easily and quickly from different perspectives. The three-dimensional contour of the scanned surface can be calculated particularly precisely due to the additional surface information, so the inventive method can also be carried out particularly easily, quickly and precisely.

The electromagnetic sensor 31 can also be positioned in some other way in the space in which the CT apparatus 7 is located, by way of example it may be secured to the ceiling or suspended therefrom or placed on a positioning device such as a tripod. By way of example the electromagnetic sensor 31 can be centrally positioned above the patient 5 or the examination table 6. Basically it is advantageous if the electromagnetic sensor 31 is positioned in such a way that the quality of the depth information about the scanned surface of the patient 5, and therewith the quality of the three-dimensional contour, is optimally homogeneous. The noise or errors from depth information ascertained by scanning, or subsequently calculated contour information should depend to the least extent possible on the depth or contour information itself or the position of the scanned region.

To determine the appropriate value of the recording parameter for a patient 5 an embodiment of the inventive imaging system in the embodiment shows here comprises a first computer 15 on which a large number of values of different recording parameters is retrievably stored, or which the computer 15 can retrieve via a network. According to an embodiment of the invention the computer 15 is designed to retrieve at least one value of a recording parameter in its internal memory. The computer 15 is also fitted with an arithmetic logic unit 22, wherein the computer 15 is designed to load a computer program into its internal memory. The computer program comprises commands which can be read by the computer 15 and is itself part of a computer program product. The computer program product can by way of example be stored on a computer-readable medium 21. The commands, which can be read by the computer 15, of the computer program are configured to carry out the inventive method if the commands are executed on the computer 15.

The computer-readable medium 21 can also be by way of example a DVD, USB stick, hard drive or a disc. The computer 15 is connected to an output unit 13, by way of example for graphical output of tomographic images. The output unit 13 is by way of example a (or several) LCD, plasma, or OLED screen(s). The computer 15 is also connected to an input unit 4. The input unit 4 is used by way of example to actuate a specific value of a recording parameter by way of user interaction, and thereby start recording of the X-ray image. The input unit 4 is by way of example a keyboard, mouse, what is known as a touchscreen, or a microphone for speech input.

The arithmetic logic unit 22 can be designed in the form of hardware and software. An interface enables the arithmetic logic unit 22 to communicate with the CT apparatus 7. In the embodiment shown here the arithmetic logic unit 22 or the computer 15 has further interfaces in order to be able to communicate with the input unit 4 or an output unit 13. The interface is a generally known hardware or software interface, e.g. the PCI bus, USB or Firewire hardware interfaces.

Figure 2:
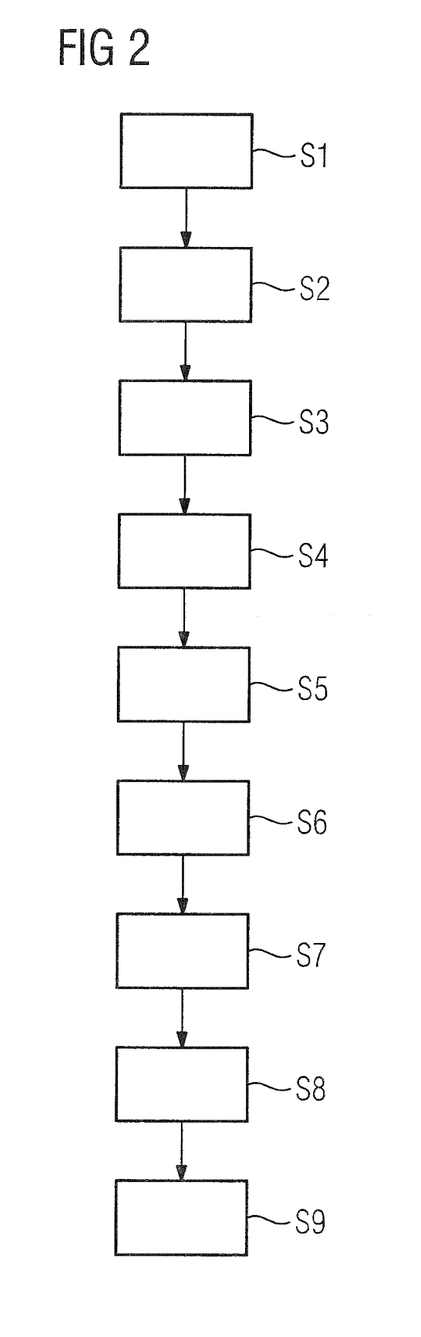
FIG. 2 shows a flow diagram of an embodiment of the inventive method.

FIG. 2 shows a flow diagram of an embodiment of the inventive method. In step S1, an embodiment of the inventive method for determining at least one value of at least one recording parameter for a recording of an X-ray image of a patient 5 positioned on an examination table 6 uses the contactless scanning of at least part of the surface of the patient 5 by way of at least one electromagnetic sensor 31, in order to calculate in step S2 the three-dimensional contour of the scanned surface without additional exposure to radiation. At least one anatomic landmark of the patient 5 is identified in step S3 using the three-dimensional contour. Current methods for identifying a landmark are by way of example what are known as "Support Vector Machines" or what are known as "Pointcloud" techniques. In step S4 the position of the anatomic landmark is determined in the coordinate system of the examination table 6. The value of the recording parameter may be determined in step S5 using the position of the anatomic landmark.

The position of the anatomic landmark in the coordinate system of the examination table 6 can be easily determined if a correlation between the coordinate system of the data recorded by the electromagnetic sensor 31 by scanning and the coordinate system of the examination table 6 or the CT apparatus 7 is known. Such a correlation can be ascertained by way of a calibration which precedes an embodiment of the inventive method.

One embodiment of the inventive method comprises in step S6 the calculation of a patient model using the three-dimensional contour for visual representation of the patient. In one embodiment, the inventive method comprises in the step S7 highlighting the identified landmark in a visual representation of the patient 5. In one embodiment of the invention, the inventive method comprises in step S8 providing a graphic user surface 23 with a button, wherein the button represents the identified landmark, wherein the button is designed to trigger determination of the value of the recording parameter by way of user interaction. In a further embodiment, the button is designed in step S9 to trigger recording of the X-ray image by way of user interaction. The inventive method can consequently be carried out particularly intuitively and quickly and the X-ray recording can be started particularly intuitively and quickly.

One advantage of an embodiment of the invention lies in that when the patient 5 moves or is relocated the corresponding values for recording parameters can be re-calculated quickly and easily. An embodiment of the inventive method can be used for preparation of recording of a topogram in order to determine the scanning region along the system axis 17 for a topogram. However, it is also capable of replacing recording of a topogram for planning recording of a diagnostic X-ray image.

The following variants of embodiments of the invention can be used during the recording of tomographic X-ray image via a CT apparatus 7 which accompanies an embodiment of the inventive method. The contour of the patient 5 and the information about the anatomic landmark or the patient model can be used to determine a value for a reconstruction parameter for reconstruction of the X-ray image from the individually recorded projections. The reconstruction parameter can be by way of example information about the surface of the patient 5 which simplifies determination of the surface of the patient 5 in the image to be reconstructed. The reconstruction center can also be determined as a function of the position of the patient 5 or a landmark. If part of the region of the patient 5, which is actually to be recorded, is located outside of the scanning region of the CT apparatus 7, so there is only an incomplete data record relating to this region, then a reconstruction in the expanded measuring field can be carried out by taking into account the information about the surface of the patient 5.

In a further variant of an embodiment of the invention, the information about the surface of the patient 5 and about the landmarks is used to improve the value for a processing parameter for subsequent image processing. The ascertained patient model is used by way of example to pass the spatial position of organs, such as the lungs or heart to an algorithm, by way of example a segmenting algorithm. At the moment image processing algorithms often have to start without initial information, whereby problems occur in particular if information is missing or incomplete. By providing additional information or initial information, which cannot be gained from the X-ray projections, an embodiment of the inventive method provides the advantage of more reliable and quicker image reconstruction or image processing.

In further embodiments single, or even all, steps of embodiments of the inventive method can be executed automatically. In the context of the present application "automatic" means that the respective step proceeds independently by way of a computer 15, and substantially no interaction of the user with the computer 15 is necessary for the respective step. In other words, the calculations which are behind the steps that are used in an embodiment of the invention are performed by the computer 15 or by the arithmetic logic unit 22. At most the user has to confirm the results calculated in the individual inventive steps or execute intermediate steps. In further embodiments of the invention, with steps carried out "fully automatically" no interaction of the user with the computer 15 is necessary at all to carry out these steps that are essential to the invention. Regardless of whether the individual steps are carried out "automatically" or "fully automatically" the inventive method can be part of a workflow which also requires the interaction of a user. The interaction with the user can consist in them manually selecting a category of scanning protocol and/or a clinical question, by way of example from a menu presented by way of the computer 15.

Figure 3:
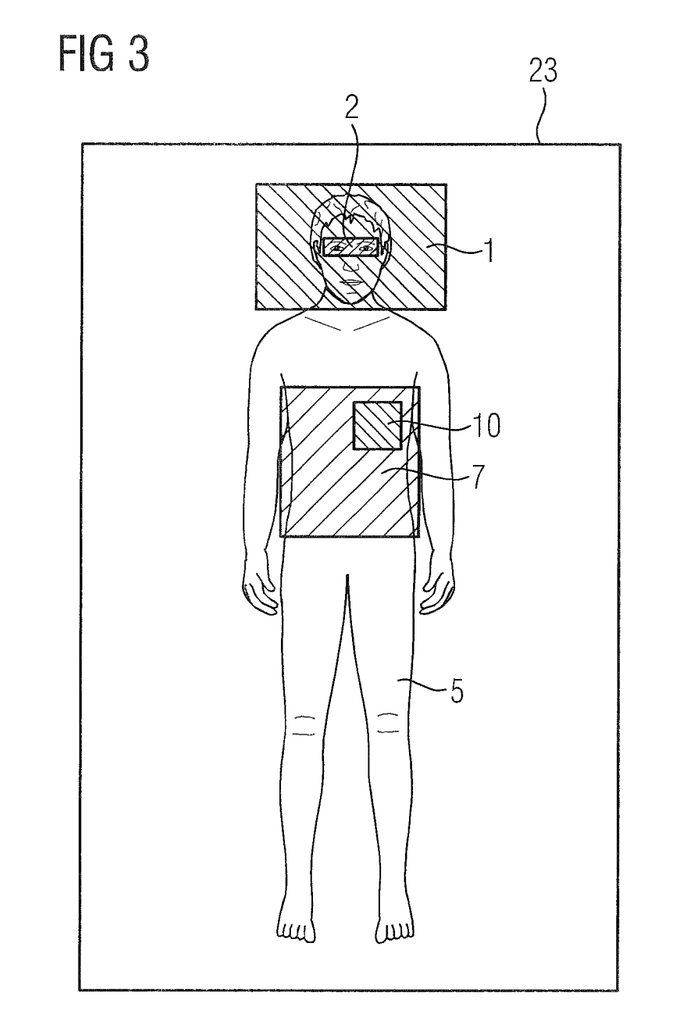
FIG. 3 shows an example graphic user surface with a visual representation of a patient.

FIG. 3 shows an example graphic user surface with a visual representation of a patient. In a first variant the visual representation of the patient 5 can be based on a patient model which has been calculated using the three-dimensional contour. In a second variant the visual representation of the patient 5 can be the direct reproduction of an image of the patient 5 taken with a camera. The depiction or highlighting of the identified landmark in the second variant can be by way of a marking or highlighting of a region in the reproduced image of the patient 5. The reproduced image of the patient 5 can, however, also be superimposed by a virtual depiction of the landmark, and this is particularly advantageous if the landmark is a region located in the body of the patient 5, by way of example an internal organ.

The graphic user surface 23 can be output on an output unit 13 by way of a computer 15. In the embodiment shown here the invention is designed to provide a graphic user surface 23 with buttons 1, 2, 7 and 10, wherein one button represents one identified landmark respectively. In the example shown here four different landmarks have been identified, namely head, eyes, thorax and the heart. If a button is activated by way of user interaction, then step S5, i.e. determination of the value of the recording parameter, is triggered. In a further embodiment of the invention the button is designed to trigger recording of the X-ray image by way of user interaction. Such a user interaction can occur by way of example by selection using a graphic pointer or on what is known as a "touchscreen".

The landmarks depicted in the graphic user surface 23 can be highlighted in various ways in different variants of embodiments of the invention. By way of example the landmarks can assume a specific color value or a specific brightness value. The corresponding features for highlighting, such as color and brightness, can also change after a user interaction. A specific feature for highlighting can also give specific information about the respective landmark. By way of example an arm, which is positioned outside of the scanning region of the CT apparatus 7, can be highlighted by a warning feature. A warning feature of this kind can occur by way of example by highlighting the respective landmark in red or by a flashing depiction of the landmark. The feature for highlighting can also change after determination of the value of the recording parameter. If the specific value of the recording parameter is above or below a certain limit value by way of example, the relevant landmark can be highlighted by a warning feature. Highlighting can also include marking the landmark, by way of example by a graphic symbol, which is displayed next to the landmark or is superimposed on the landmark.

Figure 4:
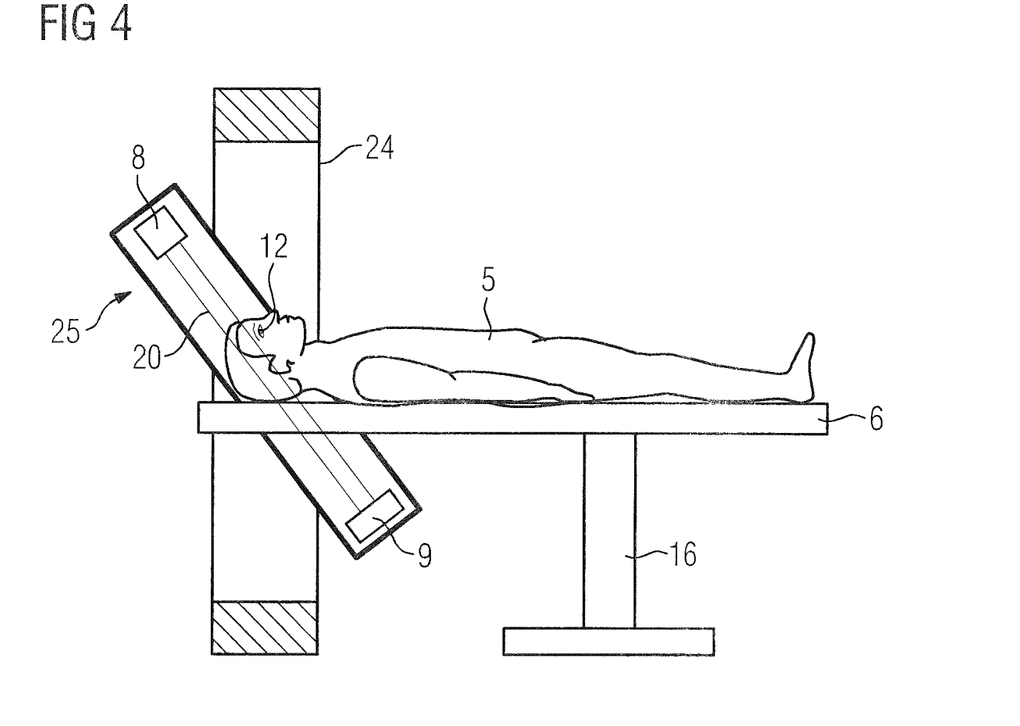
FIG. 4 shows an example embodiment of the inventive imaging system with a tiltable gantry.

FIG. 4 [shows] an example inventive imaging system with a tiltable gantry. In one embodiment of the invention, the recording is a tomographic recording by way of a CT apparatus 7, wherein the CT apparatus 7 has a tiltable gantry 19 with an X-ray source that can rotate about a system axis, wherein the anatomic landmark is a body region of the patient 5 that is particularly sensitive to radiation. Such a body region particularly sensitive to radiation can be by way of example the gonads or eyes 12. In such a case the recording parameter comprises the angle of inclination of the gantry 19, wherein the angle of inclination is determined in such a way that the body region sensitive to radiation is not located, or is located to only a limited extent, in the beam path of the X-ray source 8. Exposure to radiation for the body region of the patient particularly sensitive to radiation is reduced thereby.

In the example shown here "head" is identified in step S2 as the landmark. The recording parameter is then the angle about which the tiltable part 25 of the gantry 19 is to be tilted about a tilting axis 14 for the subsequent recording. The tiltable part of the gantry is mounted in a frame 24. In step S5 the value of the corresponding angle is then determined, so the X-rays 20 emitted by the X-ray source 8 do not penetrate the eyes 12 of the patient 5, or only penetrate them insignificantly. The value for the position of the examination table 6 is also determined as a further recording parameter in the example embodiment shown here, wherein the examination table 6 is supported by a table base 16 constructed as a foot.

In one embodiment of the invention, a warning is emitted if the specific value for the recording parameter exceeds or falls below a limit value. Such a limit value can be predefined by a user, although it may also already be retrievably stored in the internal memory of the computer 15, wherein an inventive computer program compares the specific value with the retrievably stored value to carry out embodiments of the inventive method. A warning can also be emitted if the limit value is exceeded or fallen below, wherein the warning can be emitted acoustically, visually or in some other way. The inventively determined value for the angle of the tiltable part 25 of the gantry 19 can by way of example be greater than the maximum value of the angle about which the tiltable part of the gantry 19 may be tilted. The inventive method can also analyze the position of the landmark, i.e. by way of example of the head or eyes 12, and suggest a re-positioning of the patient 5 or the identified landmark. By way of example an output with the suggestion "turn head further to the left" or "lower head further toward chest" can be emitted.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining at least one value of at least one recording parameter for a recording of an X-ray image of a patient positioned on an examination table, comprising:
    scanning, in a contactless manner, at least part of a surface of the patient using at least one electromagnetic sensor before the recording the X-ray image, the at least one electromagnetic sensor being a stereo camera, a triangulation system or a range measuring system;
    calculating a three-dimensional contour of the scanned surface using information from the at least one electromagnetic sensor;
    identifying at least one anatomic landmark of the patient using the three-dimensional contour;
    determining a position of the at least one anatomic landmark in a coordinate system of the examination table; and
    determining the at least one value of the at least one recording parameter using the determined position of the at least one anatomic landmark, the at least one recording parameter includes a reconstruction parameter, the determining the at least one value includes,
        determining a reconstruction center based on the three-dimensional contour and the determined position of the at least one anatomic landmark.

2. The method of claim 1, comprising:
calculating a patient model using the three-dimensional contour for visual representation of the patient.

3. The method of claim 2, comprising:
highlighting the identified at least one anatomic landmark in a visual representation of the patient.

4. The method of claim 3, comprising:
providing a graphic user surface with a button, the button representing the identified at least one anatomic landmark, wherein the button is configured to trigger determination of the at least one value of the at least one recording parameter via user interaction.

5. The method of claim 4, comprising:
providing a graphic user surface with a button, the button representing the identified at least one anatomic landmark, wherein the button is configured to trigger recording of the X-ray image via user interaction.

6. The method of claim 1, comprising:
highlighting the identified at least one anatomic landmark in a visual representation of the patient.

7. The method of claim 1, comprising:
providing a graphic user surface with a button, the button representing the identified at least one anatomic landmark, wherein the button is configured to trigger determination of the at least one value of the at least one recording parameter via user interaction.

8. The method of claim 1, comprising:
providing a graphic user surface with a button, the button representing the identified at least one anatomic landmark, wherein the button is configured to trigger recording of the X-ray image via user interaction.

9. The method of claim 1, wherein the determining of the at least one value of the at least one recording parameter comprises an automatic selection of a retrievably stored value of a recording parameter using at least one of the identity and the position of the at least one anatomic landmark.

10. The method of claim 1, wherein the recording parameter comprises a dose to be applied for recording of the X-ray image.

11. The method of claim 1, wherein the recording parameter comprises a volume of a contrast medium for a contrast medium-enhanced recording of the X-ray image.

12. The method of claim 1, wherein the recording parameter comprises the position of the examination table for recording of the X-ray image.

13. The method of claim 12, wherein the recording is a tomographic recording via a CT apparatus, wherein the CT apparatus comprises an X-ray source rotatable about a system axis, wherein in a specific position of the examination table the system axis centrally penetrates a region of the patient which is to be recorded.

14. The method of claim 1, wherein the recording parameter comprises an orientation of the patient.

15. The method of claim 1, wherein the recording is a tomographic recording via a CT apparatus, wherein the CT apparatus includes a liftable gantry with an X-ray source rotatable about a system axis, wherein the anatomic landmark is a body region of the patient particularly sensitive to radiation, wherein the recording parameter comprises an angle of inclination of the gantry, and wherein the angle of inclination is determined in such a way that the body region sensitive to radiation is not located, or is located only to a small extent, in a beam path of the X-ray source.

16. An imaging system, comprising:
    an X-ray apparatus configured to record an X-ray image of a patient positioned on an examination table;
    at least one electromagnetic sensor; and
    a computer including an arithmetic logic unit, the arithmetic logic unit being configured to execute computer-readable instructions to at least,
        scan, in a contactless manner, at least part of a surface of the patient using at least one electromagnetic sensor before the X-ray apparatus records the X-ray image, the at least one electromagnetic sensor being a stereo camera, a triangulation system or a range measuring system;
        calculate a three-dimensional contour of the scanned surface using information from the at least one electromagnetic sensor;
        identify at least one anatomic landmark of the patient using the three-dimensional contour;
        determine a position of the at least one anatomic landmark in a coordinate system of the examination table; and
        determine the at least one value of the at least one recording parameter using the determined position of the at least one anatomic landmark, the at least one recording parameter includes a reconstruction parameter, the determine the at least one value includes, determine a reconstruction center based on the three-dimensional contour and the determined position of the at least one anatomic landmark.

17. An imaging system, comprising:
a CT apparatus configured to tomographically record an X-ray image, the CT apparatus including a tiltable gantry with an X-ray source rotatable about a system axis;
at least one electromagnetic sensor; and
a computer including an arithmetic logic unit, the arithmetic logic unit being configured to execute computer-readable instructions to at least,
scan, in a contactless manner, at least part of a surface of a patient using at least one electromagnetic sensor before the CT apparatus records the X-ray image, the at least one electromagnetic sensor being a stereo camera, a triangulation system or a range measuring system;
calculate a three-dimensional contour of the scanned surface using information from the at least one electromagnetic sensor;
identify at least one anatomic landmark of the patient using the three-dimensional contour;
determine a position of the at least one anatomic landmark in a coordinate system of an examination table; and
determine at least one value of at least one recording parameter using the determined position of the at least one anatomic landmark, wherein the recording parameter comprises the position of the examination table for recording of the X-ray image, wherein the recording is a tomographic recording via a CT apparatus, wherein the CT apparatus comprises an X-ray source rotatable about a system axis, wherein in a specific position of the examination table the system axis centrally penetrates a region of the patient which is to be recorded, the at least one recording parameter further includes a reconstruction parameter, the determine the at least one value includes,
determine a reconstruction center based on the three-dimensional contour and the determined position of the at least one anatomic landmark.

18. An imaging system, comprising:
a CT apparatus configured to tomographically record an X-ray image, the CT apparatus including a tiltable gantry with an X-ray source rotatable about a system axis;
at least one electromagnetic sensor; and
a computer including an arithmetic logic unit, the arithmetic logic unit being configured to execute computer-readable instructions to at least,
scan, in a contactless manner, at least part of a surface of a patient using at least one electromagnetic sensor before the CT apparatus records the X-ray image, the at least one electromagnetic sensor being a stereo camera, a triangulation system or a range measuring system;
calculate a three-dimensional contour of the scanned surface using information from the at least one electromagnetic sensor;
identify at least one anatomic landmark of the patient using the three-dimensional contour;
determine a position of the at least one anatomic landmark in a coordinate system of an examination table; and
determine at least one value of at least one recording parameter using the determined position of the at least one anatomic landmark, wherein the recording is a tomographic recording via a CT apparatus, wherein the CT apparatus includes a tiltable gantry with an X-ray source rotatable about a system axis, wherein the anatomic landmark is a body region of the patient particularly sensitive to radiation, wherein the recording parameter comprises the angle of inclination of the gantry, and wherein the angle of inclination is determined in such a way that the body region sensitive to radiation is not located, or is located only to a small extent, in the beam path of the X-ray source, the at least one recording parameter further includes a reconstruction parameter, the determine the at least one value includes,
determine a reconstruction center based on the three-dimensional contour and the determined position of the at least one anatomic landmark.

19. A method for determining at least one value of at least one recording parameter for a recording of an X-ray image of a patient positioned on an examination table, comprising:
scanning, in a contactless manner, at least part of a surface of the patient using at least one electromagnetic sensor before the recording the X-ray image, the at least one electromagnetic sensor being a stereo camera, a triangulation system or a range measuring system;
calculating a three-dimensional contour of the scanned surface using information from the at least one electromagnetic sensor;
identifying at least one anatomic landmark of the patient using the three-dimensional contour;
determining a position of the at least one anatomic landmark in a coordinate system of the examination table; and
determining the at least one value of the at least one recording parameter using the determined position of the at least one anatomic landmark, the at least one recording parameter includes a dose to be applied for recording of the X-ray image, the determining the at least one value includes,
determining the dose based on the three-dimensional contour and a projection angle.

20. A method for determining at least one value of at least one recording parameter for a recording of an X-ray image of a patient positioned on an examination table, comprising:
scanning, in a contactless manner, at least part of a surface of the patient using at least one electromagnetic sensor before the recording the X-ray image, the at least one electromagnetic sensor being a stereo camera, a triangulation system or a range measuring system;
calculating a three-dimensional contour of the scanned surface using information from the at least one electromagnetic sensor;
identifying at least one anatomic landmark of the patient using the three-dimensional contour;
determining a position of the at least one anatomic landmark in a coordinate system of the examination table; and
determining the at least one value of the at least one recording parameter using the determined position of the at least one anatomic landmark, the determining the at least one value includes, determining an image processing algorithm specific to the at least one anatomical landmark based on the three-dimensional contour, the image processing algorithm corresponding to the at least one anatomical landmark.

\* \* \* \* \*